United States Patent
Nagashima et al.

(10) Patent No.: US 9,805,461 B2
(45) Date of Patent: *Oct. 31, 2017

(54) FLUOROSCOPIC IMAGE DENSITY CORRECTION METHOD, AND IMAGE PROCESSING DEVICE

(71) Applicant: FUJIFILM Corporation, Tokyo (JP)

(72) Inventors: Makiko Nagashima, Tokyo (JP); Yasunori Narukawa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/348,922

(22) Filed: Nov. 10, 2016

(65) Prior Publication Data
US 2017/0061598 A1 Mar. 2, 2017

Related U.S. Application Data

(63) Continuation of application No. 14/705,939, filed on May 6, 2015, which is a continuation of application No. PCT/JP2013/079965, filed on Nov. 6, 2013.

(30) Foreign Application Priority Data

Nov. 21, 2012 (JP) .................................. 2012-255455

(51) Int. Cl.
*G06T 7/00* (2017.01)
*G06T 7/73* (2017.01)
(Continued)

(52) U.S. Cl.
CPC ............ *G06T 7/001* (2013.01); *G01B 15/025* (2013.01); *G01N 23/04* (2013.01); *G01N 23/043* (2013.01);
(Continued)

(58) Field of Classification Search
None
See application file for complete search history.

(56) References Cited

U.S. PATENT DOCUMENTS

| | | | |
|---|---|---|---|
| 3,835,324 A | 9/1974 | Weigle | |
| 5,182,775 A * | 1/1993 | Matsui | B23K 31/12 348/125 |

(Continued)

FOREIGN PATENT DOCUMENTS

| | | |
|---|---|---|
| JP | 61-274210 | 12/1986 |
| JP | 62-277542 | 12/1987 |

(Continued)

OTHER PUBLICATIONS

"International Search Report (Form PCT/ISA/210) of PCT/JP2013/079965", dated Feb. 10, 2014, with English translation thereof, pp. 1-2, in which three of the listed references (JP2012-047569, JP62-277542 and JP61-274210) were cited.

(Continued)

*Primary Examiner* — Kim Vu
*Assistant Examiner* — Nathan Bloom
(74) *Attorney, Agent, or Firm* — JCIPRNET

(57) ABSTRACT

A reference density profile is generated in an outer circumference direction of a pipe having a reference welded portion on the basis of a reference fluoroscopic image generated from a radiation detection medium when a radiation source is disposed on a central axis of the pipe. A weld inspection density profile is generated in an outer circumference direction of a pipe having an inspection target welded portion on the basis of a weld inspection fluoroscopic image. On the basis of the reference density profile and the weld inspection density profile, density correction information is calculated. The density correction information is for correcting density irregularities in the weld inspection fluoroscopic image in the outer circumference direction of the pipe. On the basis (Continued)

of the density correction information, the density irregularities in the weld inspection fluoroscopic image are corrected.

13 Claims, 10 Drawing Sheets

(51) Int. Cl.
  *G01B 15/02* (2006.01)
  *G01B 15/04* (2006.01)
  *G01N 23/04* (2006.01)
  *G01N 21/954* (2006.01)

(52) U.S. Cl.
  CPC ........ *G06T 7/73* (2017.01); *G01N 2021/9548* (2013.01); *G01N 2223/401* (2013.01); *G01N 2223/601* (2013.01); *G01N 2223/628* (2013.01); *G01N 2223/629* (2013.01); *G06T 2207/10064* (2013.01); *G06T 2207/10121* (2013.01); *G06T 2207/30136* (2013.01); *G06T 2207/30152* (2013.01)

(56) References Cited

U.S. PATENT DOCUMENTS

| | | | |
|---|---|---|---|
| 6,137,860 A | 10/2000 | Ellegood et al. | |
| 6,377,654 B1 | 4/2002 | Willems et al. | |
| 6,466,643 B1 | 10/2002 | Bueno et al. | |
| 6,744,849 B2 | 6/2004 | Nagatsuka | |
| 8,737,682 B2 | 5/2014 | Matsumoto et al. | |
| 2003/0058991 A1 | 3/2003 | Lott | |
| 2004/0101109 A1 | 5/2004 | Shih et al. | |
| 2006/0058974 A1 | 3/2006 | Lasiuk et al. | |
| 2006/0067461 A1 | 3/2006 | Yin et al. | |
| 2009/0128557 A1* | 5/2009 | Finlayson | G01S 5/166 345/420 |
| 2011/0062349 A1 | 3/2011 | Kah | |
| 2012/0201347 A1 | 8/2012 | Prentice et al. | |
| 2012/0201348 A1 | 8/2012 | Knight et al. | |

FOREIGN PATENT DOCUMENTS

| | | |
|---|---|---|
| JP | 2003-190125 | 7/2003 |
| JP | 2005-037193 | 2/2005 |
| JP | 2012-047569 | 3/2012 |
| WO | 83/01509 | 4/1983 |

OTHER PUBLICATIONS

"Written Opinion of the International Searching Authority of PCT/JP2013/079965", dated Jan. 30, 2014, with English translation thereof, pp. 1-8, in which three of the listed references (JP2012-047569, JP62-277542 and JP61-274210) were cited.

McNamee et al., "Non-destructive Testing", Engineers Digest, Nov. 1, 1970, pp. 107-116.

"X-ray real-time imaging (XRTI) for weld inspection—3rd progress report", Rivista Italianadella Saldatura, Sep. 1, 1988, pp. 441-445.

"Search Report of Europe Counterpart Application", dated Jul. 21, 2016, p. 1-p. 8, in which the listed references were cited.

Orchard et al., "Plausibility of Image Reconstruction Using a Proposed Flexible and Portable CT Scanner", The Open Medical Imaging Journal 6 (2012), pp. 1-11.

Orchard et al., "Toward a Flexible and Portable CT Scanner", Medical Image Computing and Computer-Assisted Intervention—MICCAI 2008, Springer Berlin Heidelberg, 2008, pp. 188-195.

Redmer et al, "X-Ray Testing of Circumferential Welds by a Mechanized radiometric Weld Inspection System", 2nd Intl Conf on NDE in Relation to Structural Integrity for Nuclear and Pressuized Components, New Orleans, May 2000, NDT.net—Aug. 2000, vol. 5 No. 08, pp. 1-7.

* cited by examiner

FLUOROSCOPIC IMAGE DENSITY CORRECTION METHOD, AND IMAGE PROCESSING DEVICE

CROSS REFERENCE TO RELATED APPLICATIONS

This application is a Continuation of U.S. patent application Ser. No. 14/705,939 filed on May 6, 2015 and a Continuation of PCT International Application No. PCT/JP2013/079965 filed on Nov. 6, 2013, which claims priority under 35 U.S.C §119(a) to Patent Application No. 2012-255455 filed in Japan on Nov. 21, 2012, all of which are hereby expressly incorporated by reference into the present application.

BACKGROUND OF THE INVENTION

1. Field of the Invention

The present invention relates to a fluoroscopic image density correction method, a non-destructive inspection method, and an image processing device capable of non-destructively inspecting for defects of welded portions of pipes in a case of welding a plurality of pipes. In particular, the present invention relates to a fluoroscopic image density correction method, a non-destructive inspection method, and an image processing device capable of obtaining the same inspection results without dependency on the skill level of an inspector for identification in images even if density irregularities occur in a fluoroscopic image.

2. Description of the Related Art

There is a known method of non-destructively inspecting for defects of welded portions of pipes in a case of welding a plurality of pipes. For example, non-destructive inspection is performed as follows. First, radiation, which originates from a radiation source and is transmitted through a welded portion of pipes, is detected by a sheet-like radiation detection medium. A fluoroscopic image, which is generated by the radiation detection medium, is read from the radiation detection medium by a dedicated scanner. The read fluoroscopic image is displayed on a display screen of a personal computer (hereinafter referred to as "PC"), and an inspector checks the image visually.

In the disclosure of JP2012-47569A, an external diameter point and an inner diameter point of a pipe are detected by using a luminance profile in a direction intersecting with the pipe in a radiation fluoroscopic image of the pipe. In the disclosure of JP1987-277542A (JP-S62-277542A), a thickness of a test pipe is calculated through density comparison by performing radiographic imaging on a monitoring pipe of which a thickness is known and the test pipe of which the thickness is unknown at the same time.

In the disclosure of JP1986-274210A (JP-S61-274210A), whether sediments are present in a measurement target pipe is measured by comparing a radiation transmission measurement pattern, which is obtained by scanning the measurement target pipe, with a radiation transmission measurement pattern which is obtained by scanning a reference pipe under the same conditions.

In the disclosure of JP2005-037193A, in non-destructive inspection, an inspection target is placed on a rotational base which rotates with predetermined angular displacement, and tomography is performed by radiation. In the inspection, an eccentricity of a central axis of rotation of the inspection target is set as a parameter, and the eccentricity, which is obtained when a sharpness of a fluoroscopic image (cross-section image) is at the maximum, is specified as an optimum eccentricity of the central axis of rotation.

In the disclosure of JP2003-190125A, there is proposed image processing for facilitating comparative reading of a plurality of medical fluoroscopic images. A frequency distribution (histogram) of density values (signal values) in a reference fluoroscopic image is calculated, the density value which has the maximum frequency in the frequency distribution is calculated as a representative value, and image processing (density correction) is performed on the other fluoroscopic images such that the representative values of the other fluoroscopic images are adjusted to the representative value of the reference fluoroscopic image (paragraphs 0049 to 0055).

SUMMARY OF THE INVENTION

In a fluoroscopic image of a welded portion of pipes, not only contrasts in density caused by defects (such as bubbles and cracks) of the welded portion but also various density irregularities are exhibited. For example, distances from a radiation source are not uniform on a radiation detection medium, and thus density irregularities are caused. Further, since an amount of deviation (positioning error) from an ideal position of the radiation source is different for each inspection, density irregularities shown in the fluoroscopic image arc different for each inspection. That is, there is a following problem. In the fluoroscopic image of the welded portion of the pipes, not only various density irregularities are exhibited, but also density irregularities different for each inspection are exhibited. Thereby, identification of defects of the welded portion of the pipes greatly depends on an individual identification skill of an inspector who performs visual inspection of the fluoroscopic image. Consequently, there are following problems. In order to prevent erroneous identification, a high-level identification skill is necessary for an inspector, and determination results may be different in accordance with a skill of an inspector.

In the disclosure of JP2012-47569A, the external diameter point and the inner diameter point of the pipe are detected by using the luminance profile in the direction intersecting with the pipe. However, in the disclosure, there is no description regarding density correction of the fluoroscopic image based on the luminance profile.

In the disclosure of JP1987-277542A (JP-S62-277542A), the thickness of the test pipe is calculated through density comparison by performing radiographic imaging on the monitoring pipe of which the thickness is known and the test pipe of which the thickness is unknown at the same time. However, in the disclosure, there is no description regarding density correction of the fluoroscopic image based on the density profile. Further, in practice, it may be difficult to simultaneously perform radiographic imaging on a reference pipe and an inspection target pipe at a field site in which the pipes are welded. In this case, even if the radiographic imaging is simultaneously performed, as described above, there are various causes of density irregularities. Therefore, it is difficult to perfectly match the density irregularities shown in the fluoroscopic images on the basis of an image of the reference pipe and an image of the inspection target pipe.

In the disclosure of JP1986-274210A (JP-S61-274210A), scanning is performed on the reference pipe and the measurement target pipe under the same conditions. However, as described above, there are various causes of density irregularities. Thus, practically, it is difficult to capture fluoroscopic images of the reference pipe and the measurement target pipe under perfectly the same conditions.

In the disclosure of JP2005-037193A, it is necessary to place the inspection target on the rotational base and capture a fluoroscopic image thereof. Thus, it is difficult to apply the inspection method to a case of imaging the welded portion of the installed pipe. Further, the number and the time period of imaging operations using radiation are restricted. Therefore, it is not realistic to perform imaging several times while changing the imaging conditions.

In the disclosure of JP2003-190125A, there is proposed only a general density adjustment technique. In the technique, in density correction for medical fluoroscopic images of a human body section, the frequency distributions of density values of the fluoroscopic images are calculated, and the density values of one fluoroscopic image, which have the maximum frequencies, are adjusted to the density values of the other fluoroscopic images which have the maximum frequencies. Consequently, practically, even if such a density adjustment technique is applied to fluoroscopic images of a welded portion of the pipes by simply adjusting the density values in a specific region of one fluoroscopic image to the density values in a specific region of the other fluoroscopic images, typical density irregularities shown in the fluoroscopic image of the pipe are unlikely to be removed.

The present invention has been made in consideration of such situations, and its object is to obtain the same inspection results without dependency on the skill level of an inspector for identification in images even if density irregularities occur in a fluoroscopic image of a welded portion of pipes when inspection or measurement is performed using the fluoroscopic image of the welded portion of the pipes.

In order to achieve the object, according to an aspect of the present invention, there is provided a fluoroscopic image density correction method including: acquiring a reference fluoroscopic image generated from a flexible radiation detection medium, which is disposed on an outer circumference of a reference pipe having a reference welded portion, in case where a radiation source is disposed on a central axis of the reference pipe and radiation originating from the radiation source is detected by the radiation detection medium; generating a reference density profile, which indicates a relationship between density values and coordinates on the reference fluoroscopic image in a direction along the outer circumference of the reference pipe, on the basis of the reference fluoroscopic image; acquiring a weld inspection fluoroscopic image generated from a flexible radiation detection medium, which is disposed on an outer circumference of an inspection target pipe, in case where a radiation source is disposed inside an inspection target pipe having an inspection target welded portion and radiation originating from the radiation source is detected by the radiation detection medium; generating a weld inspection density profile, which indicates a relationship between density values and coordinates on the weld inspection fluoroscopic image in a direction along the outer circumference of the inspection target pipe, on the basis of the weld inspection fluoroscopic image; calculating weld inspection density correction information for correcting density irregularities in the weld inspection fluoroscopic image in the direction along the outer circumference of the inspection target pipe, on the basis of the reference density profile and the weld inspection density profile; and correcting the density irregularities in the weld inspection fluoroscopic image in the direction along the outer circumference of the inspection target pipe, on the basis of the weld inspection density correction information. With such a configuration, the reference density profile, which indicates a relationship between density values and coordinates in the direction along the outer circumference of the pipe, is acquired on the basis of the reference fluoroscopic image which is obtained by performing radiographic imaging on the pipe having the reference welded portion, the weld inspection density profile, which indicates a relationship between density values and coordinates in the direction along the outer circumference of the pipe, is acquired on the basis of the weld inspection fluoroscopic image which is obtained by performing radiographic imaging on the pipe having the inspection target welded portion, and density irregularities in the direction along the outer circumference of the inspection target pipe are removed from the weld inspection fluoroscopic image through correction on the basis of the reference density profile and the weld inspection density profile. Therefore, it is possible to obtain the same inspection results without dependency on the skill level of an inspector for identification in images even if density irregularities occur in the weld inspection fluoroscopic image.

According to an aspect of the present invention, in the generating of the weld inspection density profile, a density profile of a welded region and a density profile of a non-welded region are generated, in which the welded region corresponds to the welded portion of the inspection target pipe in the weld inspection fluoroscopic image, and the non-welded region corresponds to the non-welded portion of the inspection target pipe in the weld inspection fluoroscopic image, in the calculating of the weld inspection density correction information, density correction information about the welded region of the weld inspection fluoroscopic image is calculated on the basis of the density profile of the welded region, and density correction information about the non-welded region of the weld inspection fluoroscopic image is calculated on the basis of the density profile of the non-welded region, and in the correcting of the weld inspection density, density irregularities of the welded region are corrected on the basis of the density correction information about the welded region, and density irregularities of the non-welded region are corrected on the basis of the density correction information about the non-welded region. With such a configuration, even in case where density patterns of the welded portion and the non-welded portion are different, density irregularities in the outer circumference direction are reliably removed from the weld inspection fluoroscopic image.

According to an aspect of the present invention, in the generating of the weld inspection density profile, the weld inspection density profile is generated by performing curve approximation on change in the density value of the weld inspection fluoroscopic image in the direction along the outer circumference. With such a configuration, even in case where various defects occur in the welded portion, it is possible to reliably remove only density irregularities, and it is also possible to reliably leave contrast of the defects.

According to an aspect of the present invention, the fluoroscopic image density correction method further includes estimating near-radiation-source coordinates, which indicate a position on the weld inspection fluoroscopic image corresponding to a position closest to the radiation source on the radiation detection medium, on the basis of the weld inspection density profile, in which the near-radiation-source coordinates are recorded in association with at least either one of the weld inspection fluoroscopic image in which the density irregularities are corrected or the weld inspection fluoroscopic image in which the density irregularities are not corrected. With such a configuration, even after density irregularities are removed from the weld inspection fluoroscopic image, it is possible to check a position at which the density value is at the minimum due to positional deviation of the radiation source.

According to an aspect of the present invention, a diameter of the inspection target pipe is calculated on the basis of the weld inspection fluoroscopic image or the weld inspection density profile, and the diameter of the inspection target pipe is recorded in association with either one of the weld inspection fluoroscopic image in which the density irregularities are corrected or the weld inspection fluoroscopic image in which the density irregularities are not corrected. With such a configuration, in case where there is an error in the diameter of the inspection target pipe, even though the diameter of the pipe is not actually measured, it is possible to detect an actual diameter of the pipe.

According to an aspect of the present invention, the weld inspection fluoroscopic image, in which density irregularities are corrected, is displayed on a display screen, together with the reference fluoroscopic image. Thereby, it is possible to easily identify whether or not there are defects in the welded portion.

According to an aspect of the present invention, the weld inspection fluoroscopic image, in which density irregularities are corrected, is displayed on the display screen, together with the weld inspection fluoroscopic image in which density irregularities are not corrected. Thereby, it is possible to easily detect defects by visually checking the weld inspection fluoroscopic image obtained after the density irregularity correction, and it is also possible to reliably check whether or not there are defects in the weld inspection fluoroscopic image obtained before the density irregularity correction.

Further, according to an aspect of the present invention, there is provided a fluoroscopic image density correction method including: acquiring a first inspection fluoroscopic image generated from a radiation detection medium, which is disposed to face a radiation source with a welded portion of an inspection target pipe interposed therebetween, at a first inspection; generating a first inspection density profile, which indicates a relationship between a density value and coordinates of the first inspection fluoroscopic image, on the basis of the first inspection fluoroscopic image; acquiring a second inspection fluoroscopic image generated from a radiation detection medium, which is disposed to face a radiation source with the welded portion of the inspection target pipe interposed therebetween, at a second inspection; generating a second inspection density profile, which indicates a relationship between a density value and coordinates of the second inspection fluoroscopic image, on the basis of the second inspection fluoroscopic image; calculating inspection density correction information for matching relationships between the density values and the coordinates of the first inspection fluoroscopic image and the second inspection fluoroscopic image, on the basis of the first inspection density profile and the second inspection density profile; and performing density correction for matching relationships between the density values and the coordinates of the first inspection fluoroscopic image and the second inspection fluoroscopic image, on the basis of the inspection density correction information. With such a configuration, the first inspection density profile, which indicates a relationship between the density values and the coordinates, is acquired on the basis of the first inspection fluoroscopic image which is obtained by performing the first inspection (previous inspection), the second inspection density profile, which indicates a relationship between the density values and the coordinates, is acquired on the basis of the second inspection fluoroscopic image which is obtained by performing the second inspection (current inspection), and density irregularities of the inspection target pipe are removed from the second inspection fluoroscopic image (current inspection fluoroscopic image) on the basis of the first inspection density profile (the density profile of the previous inspection) and the second inspection density profile (the density profile of the current inspection). Therefore, it is possible to reliably detect occurrence of defects without dependency on the skill level of an inspector for identification in images even if density irregularities occur in the inspection fluoroscopic image.

According to an aspect of the present invention, in the generating of the first inspection density profile, the first inspection density profile is generated by performing curve approximation on change in the density value of the first inspection fluoroscopic image in a direction intersecting with the pipe, and in the generating of the second inspection density profile, the second inspection density profile is generated by performing curve approximation on change in the density value of the second inspection fluoroscopic image in a direction intersecting with the pipe. With such a configuration, even in case where various defects occur in the welded portion, it is possible to reliably remove only density irregularities, and it is also possible to reliably leave contrast of the defects.

According to an aspect of the present invention, the second inspection fluoroscopic image, in which density is corrected by the fluoroscopic image density correction method, is displayed on a display screen, together with the first inspection fluoroscopic image in which density is corrected. Thereby, it is possible to reliably identify defects which have newly occurred in the welded portion.

According to an aspect of the present invention, the first inspection fluoroscopic image and the second inspection fluoroscopic image, in which density is corrected by the fluoroscopic image density correction method, are displayed on the display screen in a reduced manner on the basis of the diameter of the calculated inspection target pipe. With such a configuration, in case where there is an error in the diameter of the inspection target pipe, even though the diameter of the pipe is not actually measured, it is possible to increase or decrease the size of the inspection fluoroscopic image to an appropriate size.

According to an aspect of the present invention, the second inspection fluoroscopic image, in which density is corrected, is displayed on the display screen, together with the second inspection fluoroscopic image in which density is not corrected.

Further, according to an aspect of the present invention, there is provided an image processing device including: a fluoroscopic image acquisition unit that acquires a reference fluoroscopic image generated from a flexible radiation detection medium, which is disposed on an outer circumference of a reference pipe having a reference welded portion, in case where a radiation source is disposed on a central axis of the reference pipe and radiation originating from the radiation source is detected by the radiation detection medium, and a weld inspection fluoroscopic image generated from a flexible radiation detection medium, which is disposed on an outer circumference of an inspection target pipe, in case where a radiation source is disposed inside an inspection target pipe having an inspection target welded portion and radiation originating from the radiation source is detected by the radiation detection medium at the time of weld inspection; a density profile generation unit that generates a reference density profile, which indicates a relationship between a density value and coordinates on the reference fluoroscopic image in a direction along the outer circumference of the reference pipe, on the basis of the reference fluoroscopic image, and generating a weld inspection density profile, which indicates a relationship between a density value and coordinates on the weld inspection fluoroscopic image in a direction along the outer circumference of the inspection target pipe, on the basis of the weld inspection fluoroscopic image; a density correction information calculation unit that calculates weld inspection density correction information for correcting density irregularities in the weld inspection fluoroscopic image in the direction along the outer circumference of the inspection target pipe, on the basis of the reference density profile and the weld inspection density profile; and a density correction unit that corrects the density irregularities in the weld inspection fluoroscopic image in the direction along the outer circumference of the inspection target pipe, on the basis of the weld inspection density correction information.

Furthermore, according to an aspect of the present invention, there is provided an image processing device including: a fluoroscopic image acquisition unit that acquires an inspection fluoroscopic image generated from a radiation detection medium which is disposed to face a radiation source with a welded portion of an inspection target pipe interposed therebetween; a density profile generation unit that generates an inspection density profile, which indicates a relationship between a density value and coordinates of the inspection fluoroscopic image, on the basis of the inspection fluoroscopic image; a density correction information calculation unit that calculates inspection density correction information for matching relationships between the density values and the coordinates of the inspection fluoroscopic image obtained at a previous inspection and the inspection fluoroscopic image obtained at a current inspection, on the basis of a first inspection density profile generated from the inspection fluoroscopic image obtained at the previous inspection and a second inspection density profile generated from the inspection fluoroscopic image obtained at the current inspection; and a density correction unit that performs density correction for matching relationships between the density values and the coordinates of the inspection fluoroscopic image obtained at the previous inspection and the inspection fluoroscopic image obtained at the current inspection, on the basis of the inspection density correction information.

According to the aspects of the present invention, it is possible to obtain the same inspection results without dependency on the skill level of an inspector for identification in images even if density irregularities occur in the fluoroscopic image of the welded portion of the pipes in case where inspection or measurement is performed using the fluoroscopic image of the welded portion of the pipes.

BRIEF DESCRIPTION OF THE DRAWINGS

FIG. 10A is a weld inspection fluoroscopic image obtained before the density irregularity correction and FIG. 10B is a weld inspection fluoroscopic image obtained after the density irregularity correction.

DESCRIPTION OF THE PREFERRED EMBODIMENTS

Hereinafter, according to the accompanying drawings, embodiments of the present invention will be described.

Density Correction of Fluoroscopic Image During Weld Inspection

First, density correction and display of a fluoroscopic image during weld inspection (inspection at the time of welding the pipe) will be described.

Figure 1A:
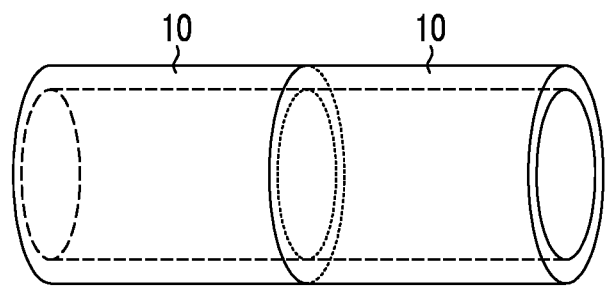
FIGS. 1A, 1B, and 1C are schematic diagrams illustrating situations of capture of fluoroscopic images during weld inspection.
Figure 1B:
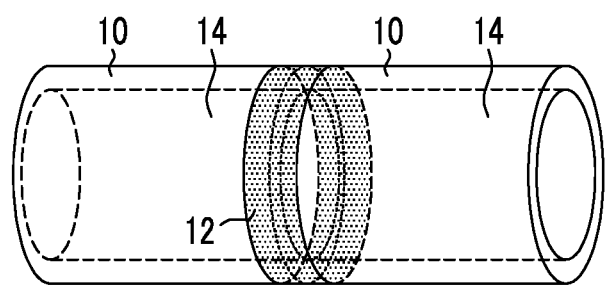
Figure 1C:
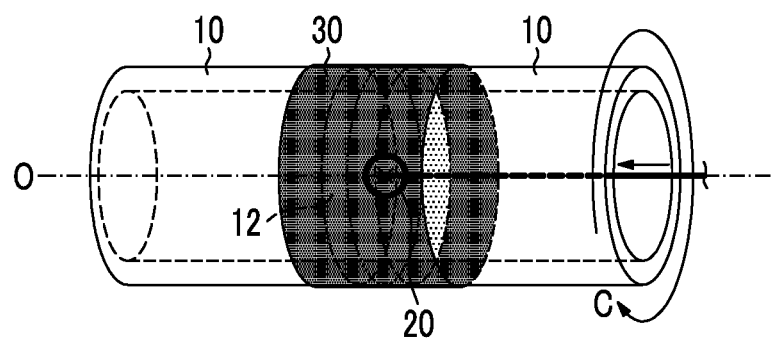

Capture of Fluoroscopic Image and Positioning Error of Radiation Source During Weld Inspection FIGS. 1A, 1B, and 1C are schematic diagrams illustrating situations of capture of fluoroscopic images during weld inspection (hereinafter referred to as "weld inspection fluoroscopic images"). FIG. 1A shows pipes 10 which are not welded. FIG. 1B shows pipes 10 which are welded. FIG. 1C shows a pipe 10 in which a radiation source 20 emitting radiation and a radiation detection medium 30 detecting radiation are disposed.

In FIGS. 1A to 1C, for convenience of description, forms of the pipes 10 and weld forms of the pipes 10 are simplified. In practice, there are various forms of the pipes 10 and various weld forms of the pipes 10. The reference numeral 12 indicates a welded portion of the pipes 10. In the present description, the "welded portion" means a welded part of the pipes 10, and includes a weld material. The radiation source 20 is ideally disposed on a central axis O of the pipe 10 as shown in FIG. 1C. The radiation detection medium 30 is flexible, and is wound around an outer circumference of the pipe 10 including the welded portion 12, as shown in FIG. 1C. As the radiation detection medium 30, in the present example, an imaging plate (stimulable phosphor film) is used. The radiation originating from the radiation source 20 is transmitted through the welded portion 12 of the pipe 10 and a non-welded portion 14 around the welded portion 12, and is detected by the radiation detection medium 30. The radiation detection medium 30 generates a weld inspection fluoroscopic image having a density pattern corresponding to a distribution of radiation intensity on the radiation detection medium 30.

Figure 2:
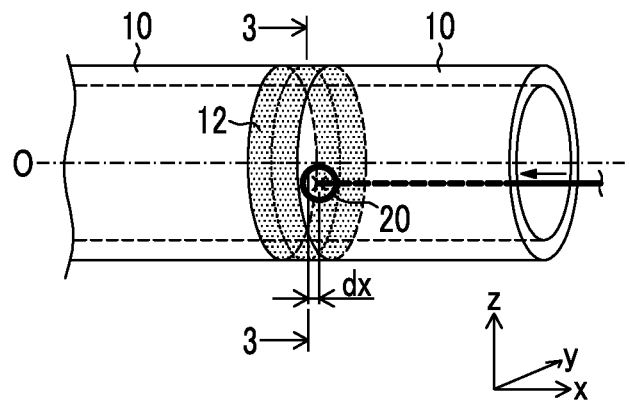
FIG. 2 is a perspective view illustrating a positioning error of a radiation source.
Figure 3:
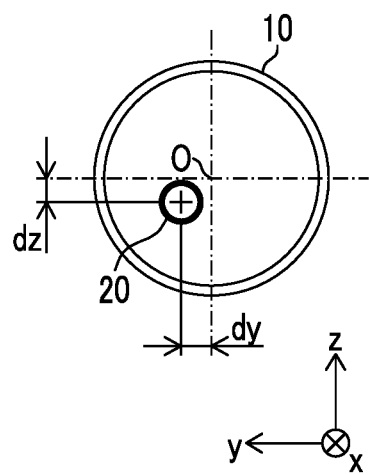
FIG. 3 is a diagram illustrating a cross-section taken along the line 3-3 of FIG. 2.

Practically, in most cases, due to various situations of the field site in which the pipes 10 are installed, the radiation source 20 may be disposed at a position deviated from the central axis O of the pipe 10, as shown in the perspective view of FIG. 2 and the cross-sectional view of FIG. 3 which shows a cross-section taken along the line 3-3 of FIG. 2.

Errors (positioning errors) between an ideal position of the radiation source 20 and a real position of the radiation source 20 are roughly classified into an error dx in a direction (length direction x) along the central axis O of FIG. 2 and errors dy and dz in the two directions (horizontal direction y, vertical direction z) which are orthogonal in the cross-section of the pipe 10 of FIG. 3. When there are such errors dx, dy, and dz, the intensity of the radiation on the radiation detection medium 30 depends on a distance from the radiation source 20. Hence, density irregularities occur in a fluoroscopic image which is generated through the radiation detection medium 30.

Density Profile During Weld Inspection

Figure 4:
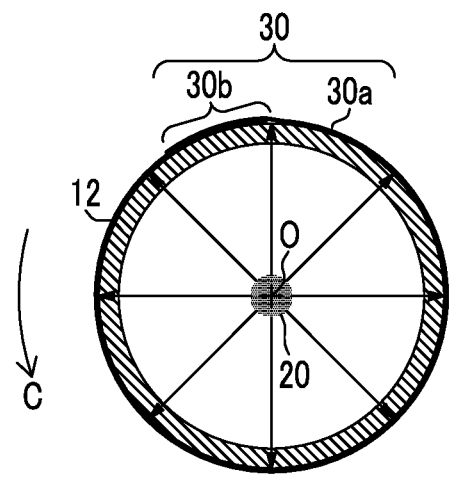
FIG. 4 is a cross-sectional view illustrating a state where the radiation source is disposed on the central axis of a welded portion of pipes.
Figure 5:
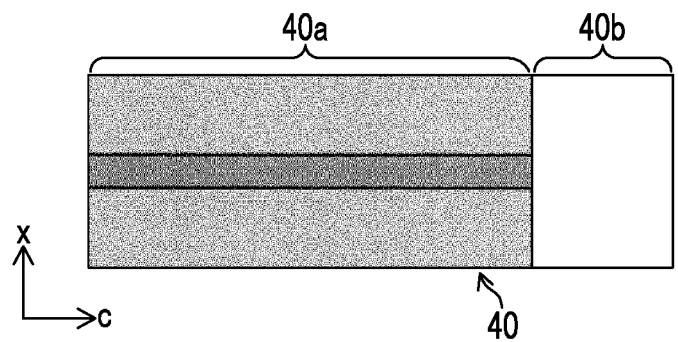
FIG. 5 is a diagram illustrating an example of a reference fluoroscopic image which is obtained through radiographic imaging in the state of FIG. 4.
Figure 6:
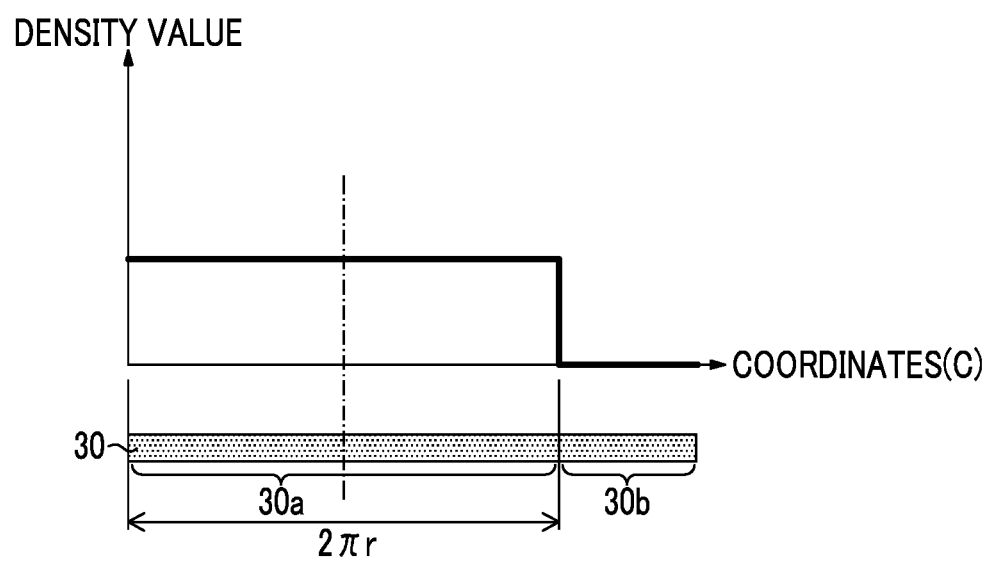
FIG. 6 is a diagram illustrating a density profile of the reference fluoroscopic image of FIG. 5.

As shown in FIG. 4, in case where the radiation source 20 is disposed at the ideal position on the central axis O of the pipe 10, for example, a fluoroscopic image 40 (hereinafter referred to as a "reference fluoroscopic image") shown in FIG. 5 is acquired. The density profile (hereinafter referred to as a "reference density profile") of a reference fluoroscopic image 40 of FIG. 5 is shown in FIG. 6. The reference density profile indicates a density pattern (a relationship between the density values and the coordinates in an outer circumference direction c) of the reference fluoroscopic image 40 in the direction (outer circumference direction c) along the outer circumference of the pipe 10. In FIG. 4, for convenience of description, it is assumed that radiation is uniformly and omnidirectionally emitted from the radiation source 20, a thickness of the welded portion 12 of the pipe 10 is uniform along the outer circumference direction c, and there are no defects in the welded portion 12.

In FIG. 4, the radiation source 20 is disposed at the ideal position on the central axis O. Therefore, there are no positioning errors dx, dy, and dz of the radiation source 20 as shown in FIGS. 2 and 3 (dx=dy=dz=0). That is, the distance from the radiation source 20 to the radiation detection medium 30 is uniformized along the outer circumference direction c. Accordingly, non-uniformity (radiation intensity unevenness) of the radiation intensity along the outer circumference direction c does not occur on the radiation detection medium 30.

In the reference fluoroscopic image 40 shown in FIG. 5, in a region 40a which corresponds to a portion (detection-effective portion 30a) of the radiation detection medium 30 having no overlap, non-uniformity (density irregularities) in density occurs in the outer circumference direction c. Here, if the thickness of the welded portion 12 is not uniform, change in density corresponding to a degree of non-uniformity occurs in the image. In the reference fluoroscopic image 40 shown in FIG. 5, a region, which is indicated by a reference numeral 40b, is a region corresponding to a portion (detection-ineffective portion 30b) of the radiation detection medium 30 having an overlap.

Figure 7:
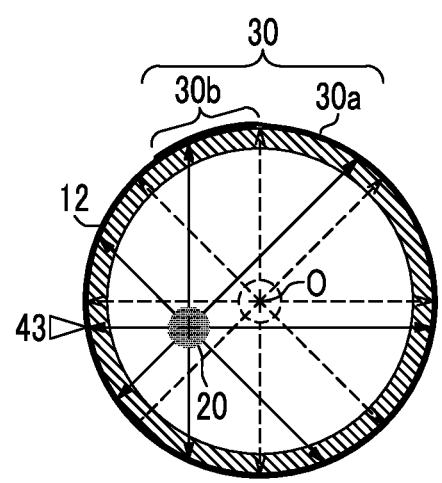
FIG. 7 is a cross-sectional view illustrating a state where the radiation source is disposed to be deviated from the central axis of the welded portion of the pipes.
Figure 8:
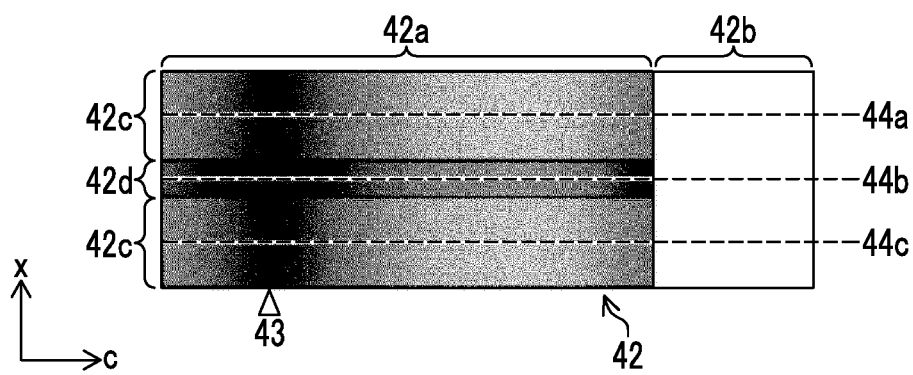
FIG. 8 is a diagram illustrating an example of a weld inspection fluoroscopic image which is obtained through radiographic imaging in the state of FIG. 7.
Figure 9:
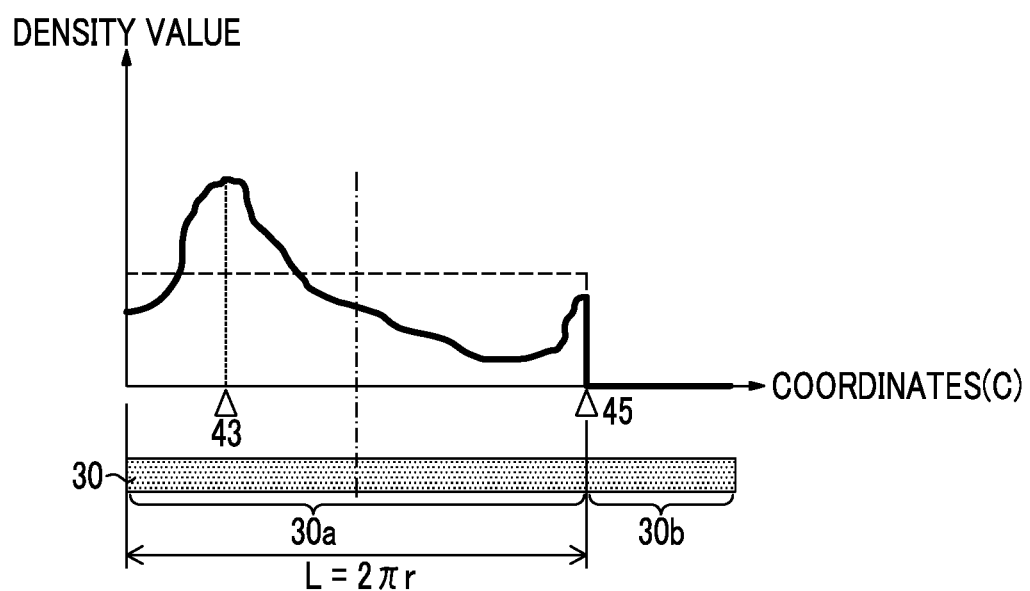
FIG. 9 is a diagram illustrating a density profile of the weld inspection fluoroscopic image of 85.

A weld inspection fluoroscopic image 42, which is obtained when the radiation source 20 is disposed to be deviated from the central axis O as shown in FIG. 7, is shown in FIG. 8. Further, the density profile (hereinafter referred to as a "weld inspection density profile") of the weld inspection fluoroscopic image 42 of FIG. 8 is shown in FIG. 9. In addition, for convenience of description, it is assumed that there is no positioning error dx in a length direction x (dx=0). Furthermore, there are no defects in the welded portion 12.

In FIG. 7, the radiation source 20 is disposed to be deviated from the central axis O. Therefore, the distance from the radiation source 20 to the radiation detection medium 30 is not uniform along the outer circumference direction c. Accordingly, non-uniformity (radiation intensity unevenness) of the radiation intensity occurs on the radiation detection medium 30. That is, even if the radiation originating from the radiation source 20 is uniformly and omnidirectionally emitted and the thickness of the welded portion 12 is uniform (constant) along the outer circumference direction c, density irregularities occur along the outer circumference direction c (horizontal direction of FIG. 8) in the weld inspection fluoroscopic image 42.

In case where defects of the welded portion 12 are detected by visually checking the weld inspection fluoroscopic image 42 shown in FIG. 8, density irregularities along the outer circumference direction c of the welded portion 12 occur. Therefore, even in case where there are defects in the welded portion 12, it is difficult to detect the defects.

Figure 10A:
FIGS. 10A and 10B are diagrams illustrating an example of density irregularity correction, where
Figure 10B:

Accordingly, in the embodiment of the present invention, density irregularities are removed through image processing from the weld inspection fluoroscopic image 42 in which there are density irregularities shown in FIG. 10A, and a weld inspection fluoroscopic image 46, in which there are no density irregularities shown in FIG. 10B, is output. Specifically, on the basis of the reference density profile shown in FIG. 6 and the weld inspection density profile shown in FIG. 9, density correction information for the weld inspection fluoroscopic image 42 with density irregularities is calculated, and density irregularity correction is performed in accordance with the density correction information. Thereby, the weld inspection fluoroscopic image 46 without density irregularities is generated.

In the weld inspection fluoroscopic image 42 shown in FIG. 8, a region, which is indicated by a reference numeral 42b, is a region corresponding to a portion (detection-ineffective portion 30b) of the radiation detection medium 30 having an overlap. Thus, the region is not shown in FIGS. 10A and 10B.

Image Processing Device used in Weld Inspection

Figure 11:
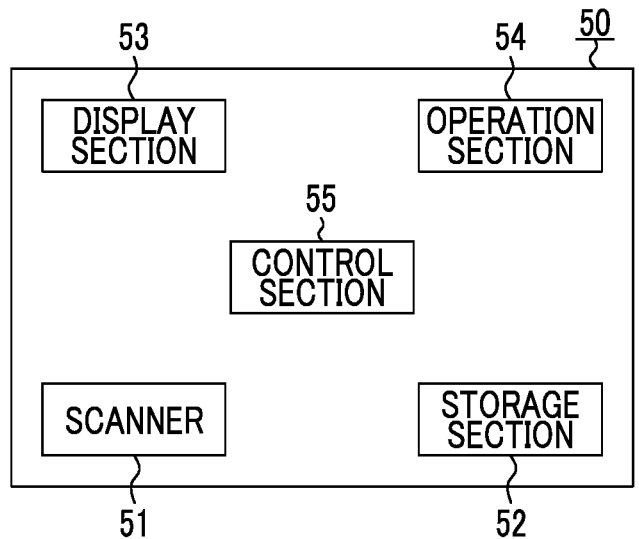
FIG. 11 is a diagram illustrating a configuration example of an image processing device.

FIG. 11 is a block diagram illustrating a configuration example of an image processing device 50 used in a fluoroscopic image density correction method according to the embodiment of the present invention.

The image processing device 50 of FIG. 11 includes: a scanner 51 (fluoroscopic image acquisition unit), a storage section 52, a display section 53, an operation section 54, and a control section 55 (density profile generation unit, density correction information calculation unit, and density correction unit).

The scanner 51 acquires fluoroscopic images (a reference fluoroscopic image and a weld inspection fluoroscopic image) from the radiation detection medium 30.

The storage section 52 stores various kinds of information including the fluoroscopic images (the reference fluoroscopic image and the weld inspection fluoroscopic image) and the density profiles (the reference density profile and the weld inspection density profile). The storage section 52 is constituted by a storage device such as a memory or a disk.

The display section 53 displays various kinds of information including the fluoroscopic images (the reference fluoroscopic image and the weld inspection fluoroscopic image) and the density profiles (the reference density profile and the weld inspection density profile). The display section 53 is constituted by a display device such as a liquid crystal display device.

The operation section 54 receives various instruction inputs. The operation section 54 is constituted by an instruction input device such as a keyboard or a touch panel.

The control section 55 is constituted by a microcomputer. The control section 55 performs various kinds of processing in accordance with a program which is stored in advance in the storage section 52.

The control section 55 has a function (density profile generation function) of generating the density profile (the reference density profile, the weld inspection density profile, and the like), as a first function. The density profile indicates a relationship between the density values and the coordinates of the fluoroscopic images (the reference fluoroscopic image, the weld inspection fluoroscopic image, and the like) in a specific direction.

During the weld inspection, the control section 55 generates the reference density profile on the basis of the reference fluoroscopic image which is generated by the radiation detection medium 30 in a state where the radiation source 20 is disposed on the central axis of the pipe 10. The reference density profile indicates at least a relationship between the density values and the coordinates on the reference fluoroscopic image in the direction c along the outer circumference of the pipe 10. Further, the control section 55 generates the weld inspection density profile on the basis of the weld inspection fluoroscopic image which is generated by the radiation detection medium 30 in a state where the radiation source 20 is disposed at a position deviated from the central axis of the pipe 10. The weld inspection density profile indicates at least a relationship between the density values and the coordinates on the weld inspection fluoroscopic image in the direction c along the outer circumference of the inspection target pipe 10.

Further, the control section 55 has a function (density correction information calculation function) of calculating density correction information, as a second function, on the basis of two different density profiles. The density correction information is for correction that matches the relationships (density patterns) between the density values and the coordinates of one fluoroscopic image and another fluoroscopic image in the specific direction.

During the weld inspection, the control section 55 calculates weld inspection density correction information, on the basis of the reference density profile and the weld inspection density profile. The information is for correcting the density irregularities in the weld inspection fluoroscopic image in the direction c along the outer circumference of the inspection target pipe 10. A specific example of the calculation will be described later.

Furthermore, the control section 55 has a function (density irregularity correction function) of correcting density irregularities in the fluoroscopic image, as a third function, on the basis of the density correction information. Here, correction of density irregularities means removal of density irregularities or reduction in density irregularities.

During the weld inspection, the control section 55 corrects the density irregularities in the weld inspection fluoroscopic image in the direction c along the outer circumference of the inspection target pipe 10, on the basis of the weld inspection density correction information.

In addition, the control section 55 has a function (fluoroscopic image display control function) of displaying the fluoroscopic image on the display section 53, as a fourth function.

Density Profile Generation During Weld Inspection

The density profile indicates a correlation (density pattern) between the density values and the coordinates of the fluoroscopic image in the specific direction.

As the density irregularities shown in the weld inspection fluoroscopic image, as described with reference to FIGS. 2 and 3, there are density irregularities caused by the positioning errors dx, dy, and dz of the radiation source 20. In the weld inspection fluoroscopic image 42 shown in FIG. 8, particularly, due to errors dy and dz along the cross-section of the pipe 10 shown in FIG. 3, the density irregularities shown along the outer circumference direction c make it difficult to visual identification as to whether or not there are defects in the welded portion 12. Therefore, the control section 55 generates the weld inspection density profile by performing curve approximation on the change in density values in the outer circumference direction c of the weld inspection fluoroscopic image 42. However, if it is determined that straight-line approximation is better than curve approximation, straight-line approximation may be performed. The curve approximation may be performed using a well-known method. Further, by calculating an average value of the density values for each pixel group with a predetermined number of pixels along the outer circumference direction c, the density profile may be temporarily generated. Furthermore, the cross-section of the pipe 10 is circular, and the radiation detection medium 30 is wound around the circumference. That is, in case where there are positioning errors dx and dy, the distance from the radiation source 20 to each position (coordinates) of the radiation detection medium 30 regularly changes along the outer circumference direction c. In accordance with the change, as density irregularities, the density values regularly increase and decrease along the outer circumference direction c. Therefore, the curve approximation is performed using regular change in density values along the outer circumferential direction c.

In the weld inspection fluoroscopic image, in case where there is a defect in the welded portion 12, a contrast is caused by the defect. However, by performing curve approximation, it is possible to obtain the weld inspection density profile which does not include the contrast caused by the defect. That is, the control section 55 generates the weld inspection density profile which does not include the contrast caused by the defect and appropriately indicates density irregularities.

Further, the control section 55 of the present example generates a density profile of a welded region 42d and a density profile of a non-welded region 42c in the weld inspection fluoroscopic image 42. Here, the "welded region" is a region corresponding to the welded portion 12 of the pipes 10 in the weld inspection fluoroscopic image 42. Further, the "non-welded region" is a region corresponding to the non-welded portion 14 of the pipes 10 in the weld inspection fluoroscopic image 42. For example, the respective density profiles are generated along a plurality of lines (only three lines 44a, 44b, and 44c are shown in FIG. 8) in the outer circumference direction c.

Likewise, the control section 55 of the present example generates the density profile of the welded region and the density profile of the non-welded region in the reference fluoroscopic image 40 through curve approximation or straight-line approximation.

Calculation of Density Correction Information During Weld Inspection

The control section 55 of the present example calculates a ratio of density values (a ratio of the density value of the weld inspection density profile to the density value of the reference density profile) at each set of the coordinates corresponding to each other in the outer circumference direction c on the basis of the reference density profile and the weld inspection density profile. Thereby, the control section 55 calculates a correction coefficient (an inverse of the ratio of the density values) for each set of the coordinates along the outer circumference direction c in the weld inspection fluoroscopic image.

Further, the control section 55 generates the density correction information about the welded region 42d on the basis of the density profile of the welded region 42d, and generates the density correction information about the non-welded region 42c on the basis of the density profile of the non-welded region 42c.

The control section 55 of the present example performs the density correction by multiplying the correction coefficient for each set of the coordinates along the outer circumference direction c by the density value of each pixel of the weld inspection fluoroscopic image.

Furthermore, the control section 55 of the present example corrects density irregularities in the welded region 42d on the basis of the density correction information about the welded region 42d, and corrects density irregularities in the non-welded region 42c on the basis of the density correction information about the non-welded region 42c.

The contrasts caused by defects such as scratches and bubbles in the fluoroscopic image are easily recognizable in the fluoroscopic image due to performing the density irregularity correction since change caused by the density irregularities along the specific direction (outer circumference direction c) is localized compared with density irregularities shown in the fluoroscopic image.

Estimation and Recording of Near-Radiation-Source Coordinates

The control section 55 of the present example calculates coordinates (near-radiation-source coordinates 43 of FIGS. 8 and 9), which indicate a position in the weld inspection fluoroscopic image 42, on the basis of the weld inspection density profile. The position corresponds to a position closest to the radiation source 20 on the radiation detection medium 30.

In the horizontal axis direction (outer circumference direction c) of the weld inspection fluoroscopic image 42 shown in FIG. 8, the coordinates at which the density is highest is the near-radiation-source coordinates. That is, in the horizontal axis direction (outer circumference direction c) of the weld inspection density profile shown in FIG. 9, the coordinates at which the density value is the maximum value is the near-radiation-source coordinates. As shown in FIG. 8, the control section 55 generates the respective density profiles along the plurality of lines (only three lines 44a, 44b, and 44c are shown in FIG. 8) in the outer circumference direction c, calculates the coordinates (maximum value coordinates) with maximum value for each density profile, and estimates the near-radiation-source coordinates 43 on the basis of the plurality of maximum value coordinates.

Further, the control section 55 records the estimated near-radiation-source coordinates in the storage section 52 in association with the weld inspection fluoroscopic image (at least one fluoroscopic image of the weld inspection fluoroscopic image in which density irregularities are corrected and the weld inspection fluoroscopic image in which density irregularities are not corrected).

Calculation and Recording of Pipe Diameter

The control section 55 of the present example calculates an outer diameter (radius) of the pipe 10 on the basis of the weld inspection fluoroscopic image or the weld inspection density profile. Further, the control section 55 records attribute information including the outer diameter r in the storage section 52 in association with the weld inspection fluoroscopic image (at least one fluoroscopic image of the weld inspection fluoroscopic image in which density irregularities are corrected and the weld inspection fluoroscopic image in which density irregularities are not corrected).

In case where the outer diameter (radius) of the pipe 10 is set as r, a length L of the portion (detection-effective portion 30a) of the radiation detection medium 30 having no overlap corresponds to the outer circumference of the pipe 10 of $2\pi r$ ($L=2\pi r$). Accordingly, the control section 55 detects coordinates of an edge 45 (a point at which the density value is suddenly lowered) of the density from the weld inspection density profile, calculates the length L of the detection-effective portion 30a of the radiation detection medium 30 corresponding to the coordinates of the edge 45 on the basis of the coordinates of the edge 45 and a resolution of the weld inspection fluoroscopic image, and calculates the outer diameter r ($=L/2\pi$) of the pipe 10 on the basis of the length L.

Example of Density Correction Processing During Weld Inspection

Next, a flow of an example of density correction processing of the fluoroscopic image during the weld inspection will be described.

Figure 12:
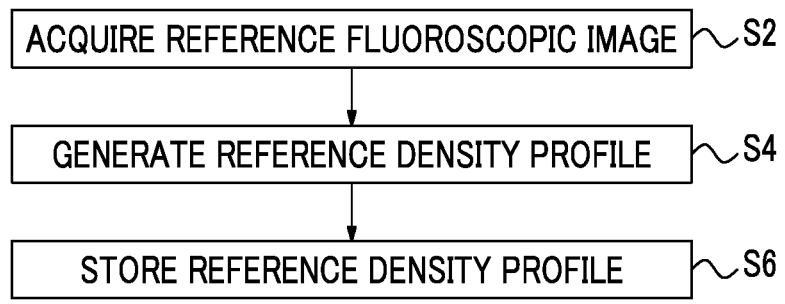
FIG. 12 is a flowchart illustrating a flow to reference profile generation.

FIG. 12 is a flowchart illustrating a flow from the reference fluoroscopic image acquisition to the reference profile storage.

First, the reference fluoroscopic image is acquired (step S2). For example, as shown in FIG. 1C, the radiation source 20 is disposed on the central axis O of the reference pipe 10, and the flexible radiation detection medium 30 is wound around the outer circumference of the welded portion 12 of the reference pipe 10. The radiation, which originates from the radiation source 20 during a constant time period and is transmitted through the welded portion 12 of the pipe 10, is detected through the radiation detection medium 30. The reference fluoroscopic image is generated through the radiation detection medium 30. Thus, the radiation detection medium 30 is removed from the welded portion 12 of the pipe 10, and a dedicated scanner 51 reads the reference fluoroscopic image from the radiation detection medium 30. Thereby, the reference fluoroscopic image 40 shown in FIG. 5 is acquired, and is stored in the storage section 52.

It should be noted that, in case where a reference fluoroscopic image is stored in the storage section 52 in advance, the reference fluoroscopic image may be acquired from the storage section 52.

Next, on the basis of the reference fluoroscopic image, the reference density profile shown in FIG. 6 is generated (step S4). The reference density profile indicates the relationship between the density values and the coordinates (density pattern) of the reference fluoroscopic image in the direction c along the outer circumference of the welded portion 12 of the reference pipe 10.

Next, the reference density profile is stored in the storage section 52 in association with the reference fluoroscopic image 40 (step S6).

Figure 13:
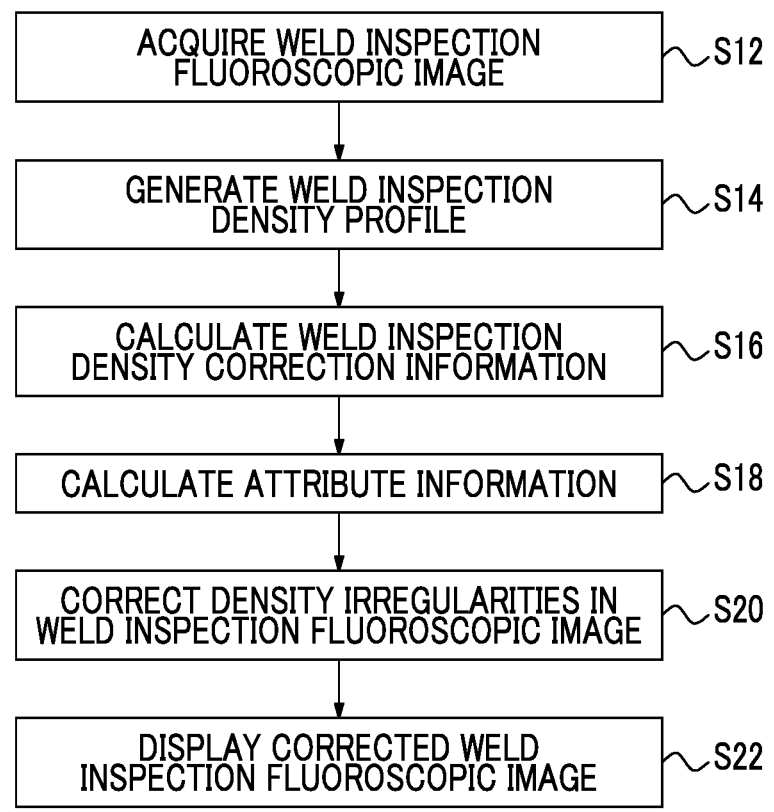
FIG. 13 is a flowchart illustrating a flow to density correction of the weld inspection fluoroscopic image.

FIG. 13 is a flowchart illustrating a flow from the weld inspection fluoroscopic image acquisition to the density correction of the weld inspection fluoroscopic image.

After a welding operation between the pipe 10 and the pipe 10 at the weld field site is performed, the weld inspection fluoroscopic image is acquired (step S12). For example, as shown in FIG. 7, the radiation source 20 is disposed inside the welded portion 12 of the inspection target pipe 10, and the flexible radiation detection medium 30 is wound around the outer circumference of the welded portion 12 of the inspection target pipe 10. The radiation, which originates from the radiation source 20 during a constant time period and is transmitted through the welded portion 12 of the pipe 10, is detected through the radiation detection medium 30. The weld inspection fluoroscopic image is generated through the radiation detection medium 30. Then, the radiation detection medium 30 is removed from the welded portion 12 of the pipe 10, and a dedicated scanner 51 reads the weld inspection fluoroscopic image from the radiation detection medium 30. Thereby, the weld inspection fluoroscopic image 42 shown in FIG. 8 is acquired.

It should be noted that, in case where a weld inspection fluoroscopic image is stored in the storage section 52 in advance, the weld inspection fluoroscopic image may be acquired from the storage section 52.

Next, on the basis of the weld inspection fluoroscopic image, the weld inspection density profile shown in FIG. 9 is generated (step S14). The weld inspection density profile indicates the relationship between the density values and the coordinates (density pattern) of the weld inspection fluoroscopic image in the direction c along the outer circumference of the welded portion 12 of the inspection target pipe 10.

Next, on the basis of the reference density profile and the weld inspection density profile, weld inspection density correction information is calculated (step S16). The information is for correcting density irregularities in the weld inspection fluoroscopic image in the direction c along the outer circumference of the inspection target pipe 10.

Next, on the basis of the weld inspection density profile, attribute information is calculated (step S18). In the present example, the outer diameter r (radius) of the inspection target pipe 10 and the near-radiation-source coordinates 43 are calculated.

Next, on the basis of the weld inspection density correction information, the density irregularities in the weld inspection fluoroscopic image in the direction c along the outer circumference of the welded portion 12 of the pipe 10 are corrected (step S20).

Next, the reference fluoroscopic image and the weld inspection fluoroscopic image, in which density irregularities are corrected, are displayed on the display section 53 (step S22).

Display of Fluoroscopic Image During Weld Inspection

The control section 55 of the present example causes a screen (display screen) of the display section 53 to display both the weld inspection fluoroscopic image, in which density irregularities are corrected, and the reference fluoroscopic image.

Further, the control section 55 of the present example causes the screen (display screen) of the display section 53 to display both the weld inspection fluoroscopic image, in which density irregularities are corrected, and the weld inspection fluoroscopic image, in which density irregularities are not corrected, in response to an instruction input from the operation section 54.

Density Correction of Fluoroscopic Image During Maintenance Inspection

Next, density correction and display of a fluoroscopic image during maintenance inspection (inspection at the time of pipe maintenance) will be described.

Figure 14:
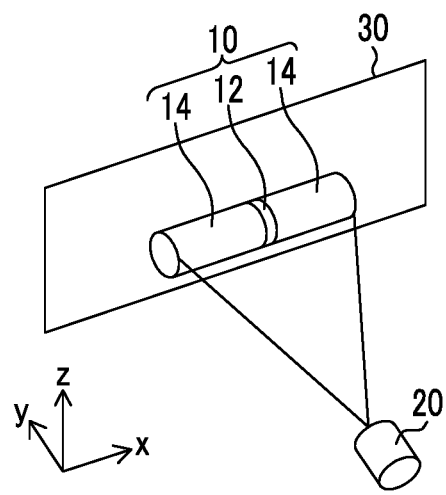
FIG. 14 is a schematic diagram illustrating a situation of capture of a fluoroscopic image during maintenance inspection.

Capture of Fluoroscopic Image and Positioning Error of Radiation Source During Maintenance Inspection FIG. 14 is a schematic diagram illustrating a situation of capture of a fluoroscopic image during maintenance inspection (hereinafter referred to as a "maintenance inspection fluoroscopic image"). As shown in FIG. 14, during the maintenance inspection, the radiation source 20 and the radiation detection medium 30 are disposed to face each other with the welded portion 12 of the inspection target pipe 10 interposed therebetween. The radiation emitted from the radiation source 20 is transmitted through the welded portion 12 of the pipe 10 and a non-welded portion 14 around the welded portion 12, and is detected by the radiation detection medium 30. The radiation detection medium 30 generates a maintenance inspection fluoroscopic image corresponding to a distribution of radiation intensity on the radiation detection medium 30.

Errors (positioning errors) between the ideal position of the radiation source 20 and the real position of the radiation source 20 are roughly classified into an error in the x direction (the length direction of the pipe 10) of FIG. 14, an error in the y direction (the direction of the distance from the radiation source 20 to the pipe 10) of FIG. 14, and an error in the z direction (the direction intersecting with the pipe 10) of FIG. 14. In case where such an error occurs, density irregularities occur in the fluoroscopic image which is generated through the radiation detection medium 30.

Density Profile During Maintenance Inspection

Figure 15:
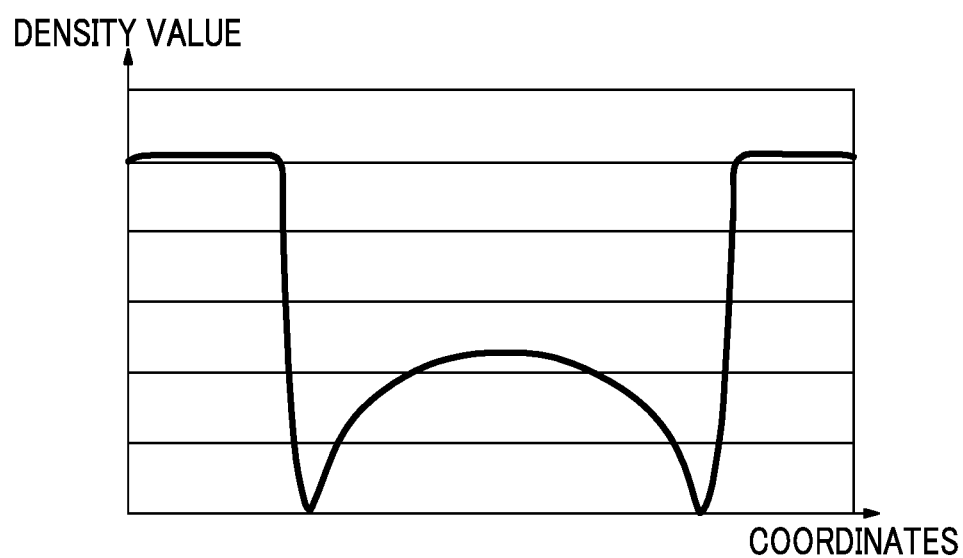
FIG. 15 is an example of a density profile of a fluoroscopic image during the maintenance inspection.

FIG. 15 shows an example of a density profile (hereinafter referred to as a "maintenance inspection density profile"). The density profile is generated by the control section 55 of the image processing device 50, on the basis of the maintenance inspection fluoroscopic image acquired from the radiation detection medium 30. The maintenance inspection density profile indicates a density pattern (a relationship between the density values and the z coordinates) in the direction z intersecting with the pipe 10.

Image Processing Device

By using the image processing device 50 shown in FIG. 11, it is possible to perform density irregularity correction of the maintenance inspection fluoroscopic image.

The scanner 51 acquires the maintenance inspection fluoroscopic image from the radiation detection medium 30. The storage section 52 stores various kinds of information including the maintenance inspection fluoroscopic image and the maintenance inspection density profile. The display section 53 displays various kinds of information including the maintenance inspection fluoroscopic image and the maintenance inspection density profile. In a manner similar to that of the above-mentioned weld inspection, the control section 55 executes various kinds of processing, in accordance with programs which are stored in the storage section 52 in advance. The control section 55 has a density profile generation function, a density correction information calculation function, a density irregularity correction function, a fluoroscopic image display control function, and the like.

During the maintenance inspection, the control section 55 generates the maintenance inspection density profile on the basis of the maintenance inspection fluoroscopic image. The maintenance inspection density profile indicates a relationship between the density values and the coordinates of the maintenance inspection fluoroscopic image in a specific direction. Further, during the maintenance inspection, the control section 55 calculates correction information (inspection density correction information) on the basis of the maintenance inspection density profile (first inspection density profile) at the previous maintenance inspection and the maintenance inspection density profile (second inspection density profile) at the current maintenance inspection. The correction information is for matching relationships between the density values and the coordinates of the previous maintenance inspection fluoroscopic image (first inspection fluoroscopic image) and the current maintenance inspection fluoroscopic image (second inspection fluoroscopic image) in the specific direction. Furthermore, during the maintenance inspection, the control section 55 performs the density irregularity correction, on the basis of the inspection density correction information. The correction is for matching relationships between the density values and the coordinates of the previous maintenance inspection fluoroscopic image and the current maintenance inspection fluoroscopic image in the specific direction.

Specific Example of Density Profile Generation

During the maintenance inspection, the radiation source 20 and the radiation detection medium 30 are disposed to face each other with the welded portion 12 of the inspection target pipe 10 interposed therebetween. In the present example, in the maintenance inspection fluoroscopic image, the horizontal direction corresponds to the x direction (the length direction of the pipe 10) of FIG. 14, and the vertical direction corresponds to the z direction of FIG. 14. In the maintenance inspection density profile shown in FIG. 15, the horizontal direction indicates the coordinates in the direction (the z direction of FIG. 14) intersecting with the pipe 10, and the vertical direction indicates the density values.

The density irregularities include density irregularities which appear along the horizontal direction (corresponding to the length direction of the pipe 10) of the maintenance inspection fluoroscopic image since the radiation source 20 is deviated from a target position (the center of the welded portion 12, for example, the contact point between the pipe 10 and the pipe 10) in the length direction (the x direction of FIG. 14) of the pipe 10. Further, the density irregularities include density irregularities which appear along the vertical direction (corresponding to the direction y intersecting with the pipe 10) of the maintenance inspection fluoroscopic image since the radiation source 20 is deviated from a target position in the direction (the y direction of FIG. 14) from the radiation source 20 toward the pipe 10. Furthermore, the density irregularities include density irregularities which appear along the vertical direction (corresponding to the z direction) of the maintenance inspection fluoroscopic image since the radiation source 20 is deviated from a target position in the z direction of FIG. 14.

The control section 55 of the present example generates the maintenance inspection density profile of the maintenance inspection fluoroscopic image. The profile indicates a density pattern (a relationship between the density values and the coordinates of the maintenance inspection fluoroscopic image) of the maintenance inspection fluoroscopic image in the specific direction.

Specific Example of Calculation of Density Correction Information

The control section 55 of the present example generates the maintenance inspection density profile shown in FIG. 15 by performing curve approximation on the change in density values in the direction (the z direction of FIG. 14) intersecting with the pipe of the maintenance inspection fluoroscopic image.

Display of Fluoroscopic Image During Maintenance Inspection

The control section 55 of the present example causes the screen (display screen) of the display section 53 to display both the fluoroscopic image (the second inspection fluoroscopic image obtained after the density correction), in which density irregularities are corrected, at the current maintenance inspection and the fluoroscopic image (the first inspection fluoroscopic image obtained after the correction), in which density irregularities are corrected, at the previous maintenance inspection.

Further, the control section 55 of the present example causes the screen (display screen) of the display section 53 to display both the current maintenance inspection fluoroscopic image (the second inspection fluoroscopic image obtained after the density correction), in which density is corrected, and the current maintenance inspection fluoroscopic image (the second inspection fluoroscopic image obtained before the density correction), in which density is not corrected, in response to an instruction input from the operation section 54.

Enlargement or Reduction of Fluoroscopic Image During Maintenance Inspection

The control section 55 of the present example enlarges or reduces the fluoroscopic image (the second inspection fluoroscopic image obtained after the density correction), in which density irregularities are corrected, at the current maintenance inspection and the fluoroscopic image (the first inspection fluoroscopic image obtained after the density correction), in which the density irregularities are corrected, at the previous maintenance inspection, on the basis of the diameter of the pipe calculated during the weld inspection, and causes the screen (display screen) of the display section 53 to display the fluoroscopic images.

Figure 16:
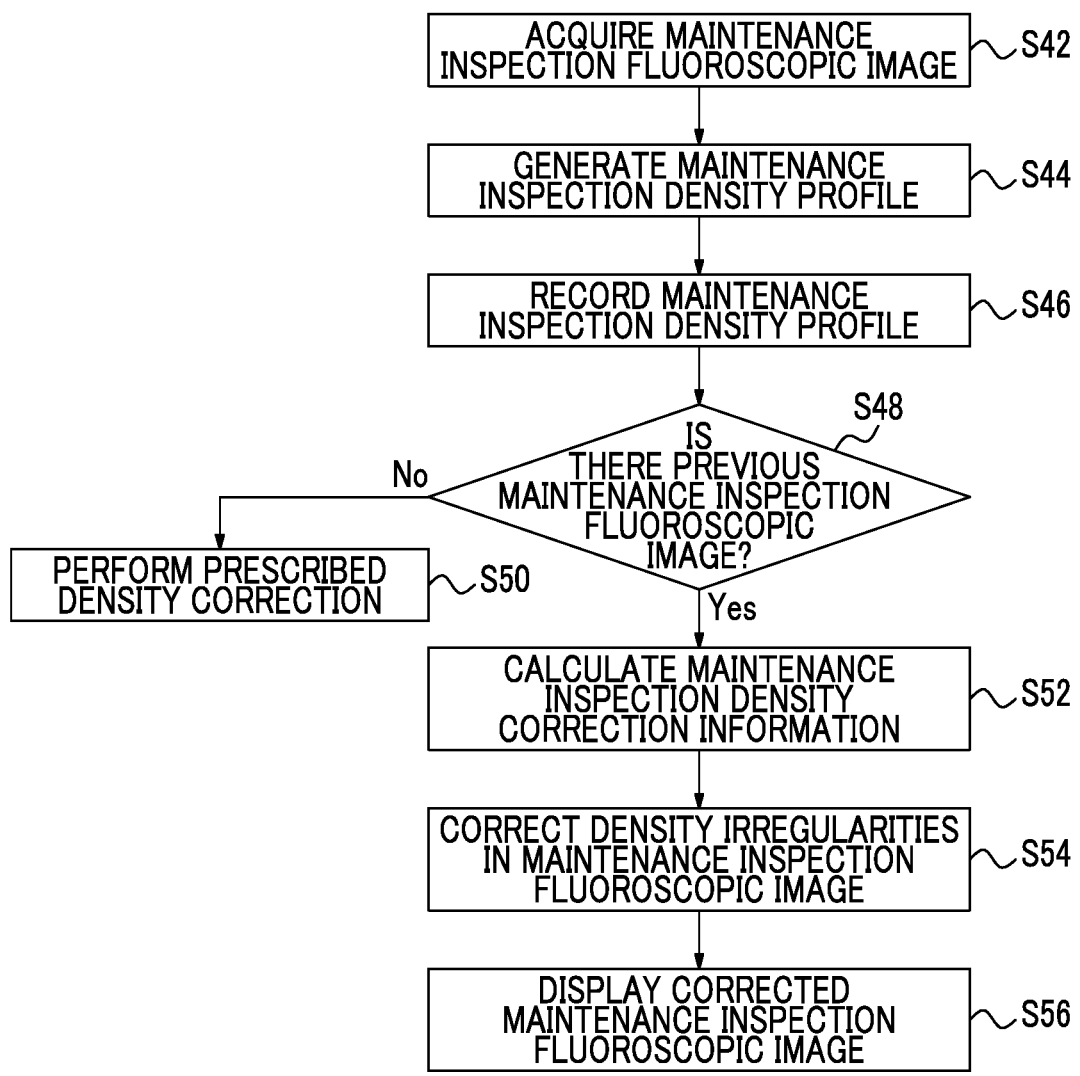
FIG. 16 is a flowchart illustrating a flow of fluoroscopic image correction processing during the maintenance inspection.

Example of Fluoroscopic Image Correction Processing During Maintenance Inspection Referring to the flowchart of FIG. 16, an example of fluoroscopic image correction processing during the maintenance inspection will be described.

First, the maintenance inspection fluoroscopic image is acquired (step S42). In the present example, as described in FIG. 14, the radiation source 20 and the sheet-like radiation detection medium 30 are disposed to face each other with the welded portion 12 of the inspection target pipe 10 interposed therebetween. Radiation is emitted from the radiation source 20 during a constant time period, and the radiation transmitted through the welded portion 12 of the pipe 10 is detected through the radiation detection medium 30 which is disposed to face the radiation source 20. Thereby, the maintenance inspection fluoroscopic image is generated through the radiation detection medium 30. The dedicated scanner 51 reads the maintenance inspection fluoroscopic image from the radiation detection medium 30, thereby acquiring the maintenance inspection fluoroscopic image, and the image is stored in the storage section 52.

Next, on the basis of the maintenance inspection fluoroscopic image, the maintenance inspection density profile shown in FIG. 15 is generated (step S44). The maintenance inspection density profile indicates a density pattern (a relationship between the density values and the coordinates) of the maintenance inspection fluoroscopic image in the specific direction (the z direction in the present example).

Next, the maintenance inspection fluoroscopic image and the maintenance inspection density profile are associated with each other and are recorded in the storage section 52 (step S46).

It is determined whether or not the fluoroscopic image at the previous maintenance inspection is present in the storage section 52 (step S48). If there is no fluoroscopic image, prescribed density correction is performed (step S50). That is, in a case of the first maintenance inspection, there is no fluoroscopic image at the previous maintenance inspection, and thus the density irregularity correction is performed on the basis of the fluoroscopic image at the current maintenance inspection.

In the second and following maintenance inspections, the current maintenance inspection fluoroscopic image is acquired in step S42, the current maintenance inspection density profile is generated in step S44, the maintenance inspection density profile is associated with the current maintenance inspection fluoroscopic image, and is recorded in the storage section 52, and a previous (first) maintenance inspection fluoroscopic image is present in the storage section 52. Therefore, processing of steps S52 to S56 is performed.

If the previous maintenance inspection fluoroscopic image is present in the storage section 52, the control section 55 calculates the maintenance inspection density correction information on the basis of the previous maintenance inspection density profile (first inspection density profile) and the current maintenance inspection density profile (second inspection density profile) (step S52). The information is for matching density patterns (relationships between the density values and the coordinates) of the current maintenance inspection fluoroscopic image and the previous maintenance inspection fluoroscopic image in the specific direction (the z direction in the present example).

Next, on the basis of the maintenance inspection density correction information, the density correction of the current maintenance inspection fluoroscopic image is performed (step S54).

Next, the current maintenance inspection fluoroscopic image obtained after the correction is displayed on the screen of the display section 53 (step S56).

It should be noted that the present invention is not limited to the examples described in the present specification and the examples shown in the drawings. It is apparent that various design changes and modifications may be performed without departing from the scope of the present invention.

What is claimed is:

1. A fluoroscopic image density correction method comprising:
    acquiring a reference fluoroscopic image generated from a radiation detection medium, which is radially disposed on the entirety of an outer circumference of a reference pipe having a reference welded portion, in case where a radiation source is disposed on a central axis of the reference pipe and radiation originating from the radiation source is detected by the radiation detection medium, wherein the reference fluoroscopic image captured at each point along a selected length of the reference pipe is a single captured image of said outer circumference at the point along the length of the reference pipe;
    generating a reference density profile, which indicates a relationship between signal values and coordinates on the reference fluoroscopic image in a direction along the outer circumference of the reference pipe, on the basis of the reference fluoroscopic image;
    acquiring a weld inspection fluoroscopic image generated from the radiation detection medium, which is radially disposed on the entirety of an outer circumference of an inspection target pipe, in case where a radiation source is disposed inside an inspection target pipe having an inspection target welded portion and radiation originating from the radiation source is detected by the radiation detection medium, wherein the weld inspection fluoroscopic image captured at each point along a selected length of the inspection target pipe is a single captured image of said outer circumference at the point along the length of the inspection target pipe;
    generating a weld inspection density profile, which indicates a relationship between signal values and coordinates on the weld inspection fluoroscopic image in a direction along the outer circumference of the inspection target pipe, on the basis of the weld inspection fluoroscopic image;
    calculating weld inspection density correction information for correcting density irregularities in the weld inspection fluoroscopic image in the direction along the outer circumference of the inspection target pipe, on the basis of the reference density profile and the weld inspection density profile; and correcting the density irregularities in the weld inspection fluoroscopic image in the direction along the outer circumference of the inspection target pipe, on the basis of the weld inspection density correction information.

2. The fluoroscopic image density correction method according to claim 1,
    wherein in the generating of the weld inspection density profile, a density profile of a welded region and a density profile of a non-welded region are generated, in which the welded region corresponds to the welded portion of the inspection target pipe in the weld inspection fluoroscopic image, and the non-welded region corresponds to the non-welded portion of the inspection target pipe in the weld inspection fluoroscopic image,
    wherein in the calculating of the weld inspection density correction information, density correction information about the welded region of the weld inspection fluoroscopic image is calculated on the basis of the density profile of the welded region, and density correction information about the non-welded region of the weld inspection fluoroscopic image is calculated on the basis of the density profile of the non-welded region, and
    wherein in the correcting of the weld inspection density, density irregularities of the welded region are corrected on the basis of the density correction information about the welded region, and density irregularities of the non-welded region are corrected on the basis of the density correction information about the non-welded region.

3. The fluoroscopic image density correction method according to claim 1, wherein in the generating of the weld inspection density profile, the weld inspection density profile is generated by performing curve approximation on change in the signal value of the weld inspection fluoroscopic image in the direction along the outer circumference.

4. The fluoroscopic image density correction method according to claim 2, wherein in the generating of the weld inspection density profile, the weld inspection density profile is generated by performing curve approximation on change in the signal value of the weld inspection fluoroscopic image in the direction along the outer circumference.

5. The fluoroscopic image density correction method according to claim 1, further comprising
estimating near-radiation-source coordinates, which indicate a position on the weld inspection fluoroscopic image corresponding to a position closest to the radiation source on the radiation detection medium, on the basis of the weld inspection density profile,
wherein the near-radiation-source coordinates are recorded in association with at least either one of the weld inspection fluoroscopic image in which the density irregularities are corrected or the weld inspection fluoroscopic image in which the density irregularities are not corrected.

6. The fluoroscopic image density correction method according to claim 2, further comprising
estimating near-radiation-source coordinates, which indicate a position on the weld inspection fluoroscopic image corresponding to a position closest to the radiation source on the radiation detection medium, on the basis of the weld inspection density profile,
wherein the near-radiation-source coordinates are recorded in association with at least either one of the weld inspection fluoroscopic image in which the density irregularities are corrected or the weld inspection fluoroscopic image in which the density irregularities are not corrected.

7. The fluoroscopic image density correction method according to claim 1, wherein a diameter of the inspection target pipe is calculated on the basis of the weld inspection fluoroscopic image or the weld inspection density profile, and the diameter of the inspection target pipe is recorded in association with either one of the weld inspection fluoroscopic image in which the density irregularities are corrected or the weld inspection fluoroscopic image in which the density irregularities are not corrected.

8. The fluoroscopic image density correction method according to claim 2, wherein a diameter of the inspection target pipe is calculated on the basis of the weld inspection fluoroscopic image or the weld inspection density profile, and the diameter of the inspection target pipe is recorded in association with either one of the weld inspection fluoroscopic image in which the density irregularities are corrected or the weld inspection fluoroscopic image in which the density irregularities are not corrected.

9. A non-destructive inspection method, wherein the weld inspection fluoroscopic image, in which density irregularities are corrected by the fluoroscopic image density correction method according to claim 1, is displayed on a display screen, together with the reference fluoroscopic image.

10. A non-destructive inspection method, wherein the weld inspection fluoroscopic image, in which density irregularities are corrected by the fluoroscopic image density correction method according to claim 2, is displayed on a display screen, together with the reference fluoroscopic image.

11. The non-destructive inspection method according to claim 9, wherein the weld inspection fluoroscopic image, in which density irregularities are corrected, is displayed on the display screen, together with the weld inspection fluoroscopic image in which density irregularities are not corrected.

12. The non-destructive inspection method according to claim 10, wherein the weld inspection fluoroscopic image, in which density irregularities are corrected, is displayed on the display screen, together with the weld inspection fluoroscopic image in which density irregularities are not corrected.

13. An image processing device comprising:
a scanner that acquires a reference fluoroscopic image generated from a radiation detection medium, which is radially disposed on the entirety of an outer circumference of a reference pipe having a reference welded portion, in case where a radiation source is disposed on a central axis of the reference pipe and radiation originating from the radiation source is detected by the radiation detection medium, wherein the reference fluoroscopic image captured at each point along a selected length of the reference pipe is a single captured image of said outer circumference at the point along the length of the reference pipe, and a weld inspection fluoroscopic image generated from the radiation detection medium, which is radially disposed on the entirety of an outer circumference of an inspection target pipe, in case where a radiation source is disposed inside an inspection target pipe having an inspection target welded portion and radiation originating from the radiation source is detected by the radiation detection medium at the time of weld inspection, wherein the weld inspection fluoroscopic image captured at each point along a selected length of the inspection target pipe is a single captured image of said outer circumference at the point along the length of the inspection target pipe;
a computer configured to
generate a reference density profile, which indicates a relationship between signal values and coordinates on the reference fluoroscopic image in a direction along the outer circumference of the reference pipe, on the basis of the reference fluoroscopic image, and generating a weld inspection density profile, which indicates a relationship between signal values and coordinates on the weld inspection fluoroscopic image in a direction along the outer circumference of the inspection target pipe, on the basis of the weld inspection fluoroscopic image,
calculate weld inspection density correction information for correcting density irregularities in the weld inspection fluoroscopic image in the direction along the outer circumference of the inspection target pipe, on the basis of the reference density profile and the weld inspection density profile; and a density correction unit that corrects the density irregularities in the weld inspection fluoroscopic image in the direction along the outer circumference of the inspection target pipe, on the basis of the weld inspection density correction information.

* * * * *